United States Patent
Adsul et al.

(10) Patent No.: US 11,261,419 B2
(45) Date of Patent: Mar. 1, 2022

(54) METHOD FOR PREPARATION OF FUNGAL MUTANT WITH HIGH HYDROLYTIC ACTIVITY

(71) Applicant: Indian Oil Corporation Limited, Maharashtra (IN)

(72) Inventors: Mukund Adsul, Haryana (IN); Simranjeet Kaur Sandhu, Haryana (IN); Reeta Rani Singhania, Haryana (IN); Anshu Shankar Mathur, Haryana (IN); Ravi Prakash Gupta, Haryana (IN); Deepak Kumar Tuli, Haryana (IN); Suresh Kumar Puri, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 96 days.

(21) Appl. No.: 16/719,630

(22) Filed: Dec. 18, 2019

(65) Prior Publication Data

US 2020/0199522 A1 Jun. 25, 2020

(30) Foreign Application Priority Data

Dec. 19, 2018 (IN) .............................. 201821048196

(51) Int. Cl.
  *C12N 1/14* (2006.01)
  *C12N 5/00* (2006.01)
  *C12R 1/80* (2006.01)

(52) U.S. Cl.
  CPC .............. *C12N 1/14* (2013.01); *C12N 5/0018* (2013.01); *C12N 1/145* (2021.05); *C12N 2500/14* (2013.01); *C12N 2500/16* (2013.01); *C12N 2500/34* (2013.01); *C12R 2001/80* (2021.05)

(58) Field of Classification Search
  CPC ........ C12N 1/14; C12N 5/0018; C12N 1/145; C12N 2500/14; C12N 2500/16; C12N 2500/34; C12N 1/38; C12N 1/22; C12N 9/2437; C12R 2001/80; C12P 21/02
  See application file for complete search history.

(56) References Cited

U.S. PATENT DOCUMENTS

2014/0363846 A1   12/2014   Edwards et al.

FOREIGN PATENT DOCUMENTS

| CN | 102559506 A | 7/2012 | |
| CN | 103045484 A | 4/2013 | |
| WO | WO-2007114729 A1 * | 10/2007 | ..... C12Y 302/01006 |

OTHER PUBLICATIONS

Lachke AH et al. Isolation of a hypercellulolytic mutant (Cu-1) of Penicillium funiculosum. 1986. Enzyme Microb. Technology, vol. 8. p. 105-108 (Year: 1986).*
Adsul MG et al. Strain Improvement of Penicillium janthinellum NCIM 1171 for increased cellulase production. 2007. Bioresource Technology. 98:1467-1473. (Year: 2007).*
El Kanouni A et al. The improvement of glucose/xylose fermentation by Clostridium acetobutylicum using calcium carbonate. 1998. World Journal of Microbiology & Biotechnology. vol. 14. 431-435. (Year: 1998).*
Zhang YP et al. Regulation of Cellulase Synthesis in Batch and Continuous Cultures of Clostridium thermocellum. 2005. Journal of Bacteriology. vol. 187, No. 1. p. 99-106.*
M. Dashtban, et al., "Fungal Bioconversion of Lignocellulosic Residues; Opportunities & Perspectives", International Journal of Biological Sciences; vol. 5, No. 6, 2009, pp. 578-595.
G. Liu, et al., "Improving Lignocellulolytic Enzyme Production with *Penicillium*: from Strain Screening to Systems Biology", Biofuels, vol. 4, No. 5, 2013, pp. 523-534.
I. V. Solov'eva, et al., "The Selection and Properties of *Penicillium verruculosum* Mutants with Enhanced Production of Cellulases and Xylanases", Microbiology, vol. 74, No. 2, 2005, pp. 141-146.

* cited by examiner

*Primary Examiner* — Paul J Holland
(74) *Attorney, Agent, or Firm* — Blank Rome LLP

(57) ABSTRACT

A method for preparing a hyper-cellulolytic catabolite derepressed mutants of ascomycetes fungus, especially variants of *Penicillium funiculosum*. Selection media used to isolate such variants include amorphous cellulose and a high concentration of glucose. Cellulase activities of mutant ID-10, in particular such as FPase and β-glucosidase were 1.5 times higher than *Penicillium funiculosum* MRJ-16 (parent). Furthermore, fungal mutant morphology was changed and no pH adjustment was required throughout the enzyme production process.

6 Claims, 1 Drawing Sheet

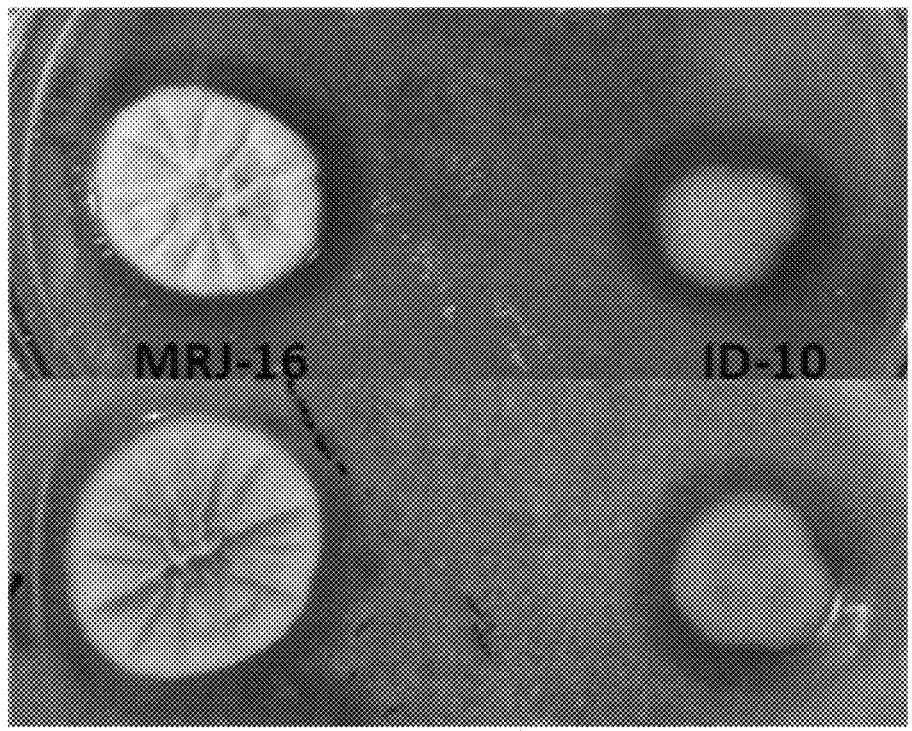

METHOD FOR PREPARATION OF FUNGAL MUTANT WITH HIGH HYDROLYTIC ACTIVITY

RELATED APPLICATION

This application claims the benefit of Indian Application No. 201821048196, filed on Dec. 19, 2018. The entire disclosure of this application is hereby incorporated by reference.

FIELD OF THE INVENTION

The present invention relates to a hyper-cellulolytic catabolite derepressed mutant of ascomycetes fungus, *Penicillim funiculosum*. The present invention also relates to a process for screening and creating hyper-cellulolytic catabolite derepressed mutants of ascomycetes fungus, especially variants of *Penicillium funiculosum* MRJ-16(parent) and ID-10 (mutant) of which ID-10(mutant) has an ability to produce higher titer of cellulases enzymes especially FPase and β-glucosidase activity than the parent *Penicillim funiculosum* MRJ-16.

BACKGROUND OF THE INVENTION

Enzymes remain a significant cost factor in cellulosic ethanol process. The development of economically viable enzyme production process with high enzyme productivity, specificity and cocktail mixture appropriate for the hydrolysis of lignocellulosic biomass can reduce the problem in commercialization of second generation biofuels. Second generation lignocellulosic biomass based biofuels are highly advantageous as the biomass is readily available, cheap and renewable. It has been stated by numerous researchers that ethanol derived from lignocellulosic biomass can decrease green house gas emission by more than 80% (Soam et al. 2016). Lignocelluloses biomass is a complex mixture of cellulose, hemicelluloses and lignin. These substrates have to undergo various pretreatment processes in order to improve the accessibility for enzymatic hydrolysis to release sugars for ethanol production. Sugars released after enzymatic hydrolysis can be converted into other platform chemicals such as butanol, methanol, dimethyl ether, succinic acid, fumaric acid, glutamic acid and sorbitol etc.

Till date there is no viable technology in India which can produce indigenous cellulases enzyme for biomass hydrolysis in cost effective manner. Lack of hyper cellulolytic microorganisms, less enzyme titer and high cost of growth media constituents are major limiting factors which in turn makes its application processes quite expensive. So, the reduction of overall enzyme production cost and development of industrially viable strain are the major goals of enzyme manufacturing industries. To economize the process, high titer of cellulolytic and hemicellulolytic enzymes, efficiency of enzyme cocktail for biomass hydrolysis, time required for enzyme production and handling of overall process are important area to focus.

Many fungal and bacterial species are efficient producers of cellulases enzymes but preferences have been given to the fungal microorganisms because of their ability to secrete complete cellulase system in the medium at high titer. Various recombinant or mutant strains of ascomycetes filamentous fungi like *Trichoderma, Penicillium, Fusarium, Humicola* and *Aspergillus* species were developed for industrial production of cellulases. Wild type fungal strains do not produce sufficient amount of cellulases enzymes required for efficient hydrolysis of lignocellulosic biomass and produce small amounts of β-glucosidase. Conventional mutational techniques have permitted the strain of *Penicillium* to be selected for hyper-producing cellulases. Fungal mutant Strains should be selected on the basis of their sensitivity to catabolite repression, easy to handle, can use cost effective carbon, nitrogen and mineral requirement and high titer of enzyme production. *Penicillium* mutant strain produces a well balanced cocktail mixture of β-glucosidase, endo-glucanases and exo-glucanase, resulting in desire performance in hydrolyzing lignocellulosic biomass. Other proteins which are vital for the hydrolysis of biomass are also secreted by this fungus.

Mutagenesis is an extensive method to improve the efficiency of fungi to secrete cellulose degrading enzyme at high titer. Mutagenesis technique include physical mutagens like UV-light, gamma rays, X-rays, infra-red rays etc and chemical mutagens like methyl nitrosoguanidine, nitrous oxide, ethyl-methane-sulphonate, hydroxylamine, dimethyl sulphate etc. Jafari N et al (2017) has improved the cellulolytic activity of *Aspergillus niger* using UV-light, resulting in the mutant with two fold increase in filter paper activity (FPA). Similarly, cellulase and xylanase activities in *Penicillium verruculosum* 28K mutants were improved about 3-fold using four cycles of UV mutagenesis. The enzyme production was further improved by 2- to 3-fold in a two-stage fermentation process using wheat bran, yeast extract medium and microcrystalline cellulose as the inducer (Solov'eva IV et al. 2005). *Trichoderma atroviride* mutants were created by mutagenesis using N-methyl-N'-nitro-N-nitrosoguanidine (NTG) as well as UV-light by Kovács and et al. (2008). These *T. atroviride* mutants (e.g. *T. atroviride* TUB F-1724) produce high levels of β-glucosidase and extracellular cellulases using pretreated willow. In another study, the catalytic efficiency and optimum pH of *T. reesei* endo-β-1,4-glucanase II were improved by saturation mutagenesis followed by random mutagenesis and two rounds of DNA shuffling. The pH optimum of the variant (Q139R/L218H/W276R/N342T) was shifted from 4.8 to 6.2, while the enzyme activity was improved more than 4.5-fold (Qin Y et al. 2008).

US 2014/0363846 describes the process for cellulases enzyme production using fungal cells of genus *Myceliophthora* by submerged fermentation and soluble non cellulase-inducing carbon sources were used. Carbon sources used were glucose, glycerol, xylose, glucose: xylose (90:10), sucrose, glucose and inducing substrate like sophorose, gentibiose and cellobiose, molasses, fructose and glucose: fructose (50:50). Similar protein and Filter paper activity (FPU) was observed when glucose alone and with inducing substrate was used as carbon sources. Maximum of average 0.55 FPU/mg proteins was observed when xylose was used. Claimants of the patent mentioned about the variety of cellulases, hemicellulases, lignin degrading enzymes, estrases, swollenin, expansins and many more additional enzymes secreted by the *Myceliophthora thermophila* strain (ATCC No. 42464) used but didn't present any of the activity of above these in patent expect Filter paper activity.

CN103045484B mentioned the production of cellulases enzyme using *Penicillium decumbens* (CCTCC M2011195) mutant strain. A mutant strain was developed using UV irradiation and a chemical mutagen NTG (N-methyl-N'-nitro-N-nitrosoguanidine). The fermentation medium was composed of fishing xylose, wheat bran, microcrystalline cellulose, ammonium sulfate, potassium phosphate monobasic and magnesium salt. Enzyme activity obtained was filter paper 10 IU/ml, endoglucanase activity 30 IU/ml, exo-glucanase activity 1.5 IU/ml and β-glucosidase 8 IU/ml. The enzyme cocktail produced by the researchers will be insufficient if used for biomass hydrolysis because of low β-glucosidase titer in comparison to filter paper activity, thus more enzymes need to be doped. Furthermore, the choice of carbon source as fishing xylose and nitrogen source as wheat bran may makes this process rather uneconomical and non-sustainable.

Patent application no. CN102559506A (2013), *Penicillium oxalicum* CGMCC No. 4357 strain was isolated and identified to produce cellulases enzymes using corn stover flour as carbon source. They claim that the process of enzyme production was fast (7 days) with shaking cultured to reach peak endoglucanases, exoglucanases and β-glucosidase activity of 228.17 IU/ml, 109.90 IU/ml and 81.45 IU/ml respectively. Enzyme was used for corn stover straw saccharification at 9% (w/v) cellulose concentration; saccharification rate was calculated to be more than 80% when 25 ml of enzyme (50% of total volume) was used. The amount of enzyme used by the claimants is very high and substrate concentration is low, which is not economically viable for industrial scale process.

SUMMARY OF THE INVENTION

The present invention relates to creating hyper-cellulolytic catabolite de-repressed mutant of ascomycetes fungus, especially variant of *Penicillium funiculosum* MRJ-16, where higher D-glucose level cannot inhibit the enzymes secretion. The present invention further relates to creating hyper-cellulolytic catabolite de-repressed mutants of ascomycetes fungus, especially variant of *Penicillium funiculosum*, which has an ability to produce higher titer of cellulases enzymes especially FPase and β-glucosidase activity than the parent *Penicillim funiculosum* MRJ-16 mutant strain developed earlier in lab and under patent protection. The present invention also relates to a method for producing cellulases and/or hemi-cellulases using the mutant microorganisms, and to a method for degrading or saccharifying biomass using the secreted enzymes. It was observed that since, the amount of enzyme use for saccharification of biomass was reduced; this will bring down the production cost of industrial process which utilizes sugar released after saccharification to produce valuable products eg. Bioethanol.

BRIEF DESCRIPTION OF DRAWINGS

FIG. 1. *Penicillium funiculosum* MRJ-16 (parent) and ID-10 mutant colony on screening media plate

DETAILED DESCRIPTION OF THE INVENTION

The present invention discloses a mutant fungal strain derived from *Penicillim funiculosum* MRJ-16, which has an ability to produce higher titer of cellulases enzymes especially FPase and β-glucosidase activity than the parent *Penicillim funiculosum* MRJ-16. The present invention in particular discloses a mutant fungal strain *Penicillim funiculosum* ID-10 (acc no. MTCC 25224 deposited on Oct. 23, 2018, at the Institute of Microbial Technology WITCH), Sector 39A, Chandigarh-160036, India), which possesses different growth, morphology and cellulose hydrolyzing properties in the presence of glucose than the parent strain from which it was derived.

Present invention also discloses a method of preparing a mutant fungal strain from MRJ-16 which comprises: subjecting *Penicillium funiculosum* MRJ-16 to aerobic culture media followed by treatment with UV light and/or NTG (N-methyl-N'-nitro-N-nitrosoguanidine) and/or EMS (Ethyl methanesulfonate) and screening colonies for higher cellulolytic activity followed by several more mutations.

Another aspect of the present invention discloses a method of selection of mutual fungal strain by visually selection on basis of cream colored pigmentation and measuring the amorphous cellulose hydrolyzed zone.

In accordance with the present invention, a mutant strain, *Penicillium funiculosum* ID-10, characterized by (A) higher cellulase activity than *Penicillium funiculosum* MRJ-16 (parent strain) and (B) much higher β-glucosidase activity obtained by subjecting *Penicillium funiculosum* MRJ-16 to aerobic culture media followed by treatment with UV light and/or NTG and or EMS and screening colonies for higher cellulolytic activity followed by several more mutations. The process of screening mutant was done using solid media comprises amorphous cellulose ranging from 0.1% to about 0.4% and a catabolite repressor molecule like glucose and or xylose. Mutants were selected by measuring the diameter of hydrolyzed zone. Enzyme production from *Penicillium funiculosum* ID-10 mutant strain was done using cellulose or pretreated lignocellulosic biomass (rice straw, wheat straw or baggase) as carbon source. The enzyme preparation produced has mixture of necessary enzyme such as FPase, CMCase, Cellobiase, β-glucosidase, α-L arabinofuranosidase, β-xylosidase, cellobiohydrase, oxidases or mixture thereof. A part of enzyme produced is harvested and used as it was without downstream processing ie enzyme along with fungal mycelia and another part of enzyme was separated from mycelia, concentrated and used for pretreated lignocellulosic biomass saccharification.

Having described the basic aspects of the present invention, the following non-limiting examples illustrate specific embodiment thereof.

Example No. 1—Screening of an Efficient Mutant for Enzyme Production

The parent strain *Penicillium funiculosum* MRJ-16 mutant strain was used to create mutants for enzyme production. Mutations were done using UV or NTG or EMS mutagens alone or all together. The mutant strains were obtained after repeated multistage mutagenesis process. Mutants were selected sequentially on specially designed media containing amorphous cellulose and glucose at different concentration from 1-4% (w/w) (screening media composition in table no. 1). Mutant strain that hydrolyzes the amorphous cellulose in the presence of 4% glucose was selected after visualizing and measuring the hydrolyzed zone. Stability of mutant stain for enzyme production capability was tested for multiple cycles and then used for further study.

TABLE NO. 1

| | Screening media composition | |
|---|---|---|
| S. No. | Chemical Components | Quantity (g/L) |
| 1 | Ammonium sulphate | 1.4 |
| 2 | $KH_2PO_4$ | 2.0 |
| 3 | $MgSO_4 \cdot 7H_2O$ | 0.3 |
| 4 | $CaCl_2 \cdot 3H_2O$ | 0.3 |
| 5 | Urea | 0.3 |

TABLE NO. 1-continued

Screening media composition

| S. No. | Chemical Components | Quantity (g/L) |
|---|---|---|
| 6 | Tween-80 | 0.1 |
| 7 | Peptone | 0.25 |
| 8 | Yeast Extract | 0.10 |
| 9 | $ZnSO_4 \cdot 7H_2O$ | 0.0014 |
| 10 | $FeSO_4 \cdot 7H_2O$ | 0.005 |
| 11 | $MnSO_4 \cdot H_2O$ | 0.0016 |
| 12 | $CoCl_2 \cdot 6H_2O$ | 0.002 |
| 13 | Glucose | 30-40 |
| 14 | Amorphous cellulose | 1-4 |
| 15 | Agar | 20 |
| 16 | pH | 5.0 |

The visual observation of the *Penicillium funiculosum* MRJ-16 (parent) and mutant (ID-10) cultured on screening media plate showed that in the presence of 4% glucose, ID-10 mycelia remains cream colored till 10-13 days of incubation, while MRJ-16 started turning yellow before the onset of spores as shown in FIG. 1. More wrinkled surface was observed in case of MRJ-16 than ID-10. ID-10 produces small colony with wide hydrolysis zone than MRJ-16 mutant with colony diameter and hydrolyzed zone diameter of 12 mm and 20 mm respectively.

Example No. 2—Enzyme Production Comparison of Mutant ID-10 and MRJ-16 Parent Strains Fermentation process was carried out in aerated stirred tank bioreactor of 2 L glass jacketed vessel, with 1.8 L working volume. The media components of fermentation media used were ammonium sulphate 3.5 g/L, $KH_2PO_4$ 4 g/L, $MgSO_4.7H_2O$ 0.5 g/L, $CaCO_3$ 2.5 g/L, Glycerol 2.5 g/L, Corn steep solids 20 g/L, cellulose 20 g/L and Tween-80 2 ml/L. The fermenter containing 1.5 L medium was sterilized at 120° C. for 20 min. After cooling, the temperature was kept at 30° C., pH adjusted to 5.5 and inoculated with 10% active liquid seed (seed media composition in table no.2) of *Penicillium* ID-10 mutant strain. After 96 h of fermentation, the enzyme broth was collected, centrifuged and analysis of clear enzyme broth was done.

TABLE NO. 2

Seed/Inoculum Media composition

| S. No. | Chemical Components | Quantity (g/L) |
|---|---|---|
| 1 | Ammonium Sulphate | 4 |
| 2 | $KH_2PO_4$ | 3 |
| 3 | $MgSO_4 \cdot 7H_2O$ | 0.1 |
| 4 | $CaCO_3$ | 2 |
| 5 | Sucrose | 5 |
| 6 | Corn Steep Liquor | 15 |
| 7 | Cellulose | 10 |
| 8 | Tween-80 | 2 |
| 9 | pH | 5.5 |

The results obtained after 96 hr of incubation were; parent MRJ-16 produces 15 g/L of protein, 62 IU/ml of β-glucosidase and 6.4 FPU/ml of filter paper activity, while ID-10 produces 16 g/L of protein, 87 IU/ml of β-glucosidase and 9.3 FPU/ml of filter paper activity.

Example No. 3—Enzyme Production Comparison of Mutant ID-10 and MRJ-16 Parent Strains Fermentation process was carried out in aerated stirred tank bioreactor of 2 L glass jacketed vessel, with 1.8 L working volume. The media components of fermentation media used were ammonium sulphate 5 g/L, $KH_2PO_4$ 6 g/L, $MgSO_4.7H_2O$ 1 g/L, $CaCO_3$ 5 g/L, Glycerol 2.5 g/L, Corn steep solids 30 g/L, cellulose 30 g/L and Tween-80 2 ml/L. The fermenter containing 1.5 L medium was sterilized at 120° C. for 20 min. After cooling, the temperature was kept at 30° C., pH adjusted to 5.5 and inoculated with 10% active liquid seed (seed media composition in table no. 3) of *Penicillium* ID-10 mutant strain. After 96 h of fermentation, the enzyme broth was collected, centrifuged and analysis of clear enzyme broth was done.

TABLE NO. 3

Seed/Inoculum Media composition

| S. No. | Chemical Components | Quantity (g/L) |
|---|---|---|
| 1 | Ammonium Sulphate | 5 |
| 2 | $KH_2PO_4$ | 6 |
| 3 | $MgSO_4 \cdot 7H_2O$ | 1 |
| 4 | $CaCO_3$ | 2.5 |
| 5 | Sucrose | 10 |
| 6 | Corn Steep Liquor | 10 |
| 7 | Cellulose | 20 |
| 8 | Tween-80 | 2 |
| 9 | pH | 5.5 |

The results obtained after 96 hr of incubation were; parent MRJ-16 produces 16.2 g/L of protein, 64 IU/ml of β-glucosidase and 6.2 FPU/ml of filter paper activity, while ID-10 produces 16 g/L of protein, 98 IU/ml of β-glucosidase and 10.2 FPU/ml of filter paper activity.

Example No. 4—Enzyme Production in the Presence of Glucose

In order to demonstrate the glucose repression on enzyme production, cellulose used as carbon source was replaced with glucose. Enzyme production from *Penicillium funiculosum* ID-10 mutant strain was carried out under the conditions and media composition as described in example no.2 and 3 except cellulose. Concentrated solution of glucose was autoclaved separately and added into media at 4% w/v concentration. Fermentation was lasted approximately for 120 h, enzyme harvested and analyses were done (Table 5).

TABLE NO. 4

Enzyme production from MRJ-16 and parent strain in the presence of glucose

| Mutants | Concentration (% w/v) | FPU/ml | BGL (IU/ml) |
|---|---|---|---|
| *Penicillium funiculosum* MRJ-16 mutant (Parent strain) | Cellulose 3% | 6.47 | 62 |
| | Glucose 4% | 0.12 | ND |
| *Penicillium funiculosum* ID-10 | Cellulose 3% | 10.3 | 97 |
| | Glucose 4% | 3.21 | 29 |

Example No. 5—Diversity of Enzyme Secreted

Cellulases enzymes production using *Penicillium funiculosum* ID-10 mutant strain was performed according to example no.2. The secretome analyses were done it is comprise enzyme activities of β-glucanase 87 IU/ml, Filter paper activity 9.3 FPU/ml, endoglucanase 125 IU/ml, α-L arabinofuranosidase 0.05 IU/ml, β-xylosidase 1.2 IU/ml, xylanase 227 IU/ml, pectinase 97 IU/ml and oxidases 6.54 IU/ml analyzed using respective substrates.

Example No. 6—Diversity of Enzyme Secreted

Cellulases enzymes production using *Penicillium funiculosum* ID-10 mutant strain was performed according to example no.3. The secretome analyses were done it is comprise enzyme activities of β-glucosidase 98 IU/ml, Filter paper activity 10.2 FPU/ml, endoglucanase 132 IU/ml, α-L arabinofuranosidase 0.05 IU/ml, β-xylosidase 1.2 IU/ml, xylanase 247 IU/ml, pectinase 95 IU/ml and oxidases 5.23 IU/ml analyzed using respective substrates.

Example No. 7—Hydrolysis of Pre-Treated Lignocellulosic Biomass Using Enzyme as Such The efficiency of enzyme produced was determined by its ability to hydrolyze lignocellulosic biomass such as acid pretreated rice straw and produce sugars. Enzyme broth produced in example no.6 was used as such without any downstream processing. Hydrolysis was performed at high substrate loading of biomass i.e. 20% at pH 4-5, 50 mM citrate buffer, temperature 50° C. at enzyme loadings of 6 FPU/g of dry biomass. Sugars released were determined at regular interval of time by HPLC. Enzyme cocktail worked efficiently and leads to 63% glucan conversion in 48 h.

The invention claimed is:

1. A method of preparing a mutant fungal strain comprising:
   (a) preparing a mutant fungal strain by contacting *Penicillium funiculosum* MRJ-16 with an aerobic culture medium followed by treatment with UV light or N-methyl-N'-nitro-Nnitrosoguanidine (NTG) or ethyl methanesulfonate (EMS) mutagens or in combination;
   (b) screening for the mutant fungal strain having higher celluloytic activity as compared to the *Penicillium funiculosum* MRJ-16 by aerobic fermentation in an aerobic culture medium comprising amorphous cellulose and glucose at concentration of 1-4% (w/w) under conditions suitable for the production of enzymes;
   (c) obtaining a mutant fungal strain *Penicillium funiculosum*-ID-10; and
   (d) screening the efficiency of the enzyme produced by the mutant fungal strain *Penicillium funiculosum*-ID-10 by hydrolyzing biomass.

2. The method in of claim 1, wherein the aerobic culture medium comprises 4% glucose.

3. The method in of claim 1, wherein the fermentation in step (b) is carried in an aerated stirred tank having a glass jacketed vessel of 2 L and working volume of 1.8 L.

4. The method in of claim 1, wherein the aerobic culture medium comprises ammonium sulphate 5 g/L, $KH_2PO_4$ 6 g/L, $MgSO_4 \cdot 7H_2O$ 1 g/L, $CaCO_3$ 5 g/L, Glycerol 2.5 g/L, Corn steep solids 30 g/L, cellulose 30 g/L and Tween-80 2 ml/L.

5. The method of claim 1, wherein the method is carried out in a fermenter, which was sterilized at 120° C. for 20 minutes and cooled at 30° C. along with maintaining pH of 5.5.

6. The method of claim 1, wherein the enzyme produced in step (b) is a cellulase enzyme.

* * * * *